(12) United States Patent
Lee-Chen et al.

(10) Patent No.: US 10,213,470 B2
(45) Date of Patent: Feb. 26, 2019

(54) METHOD FOR TREATING SPINOCEREBELLAR ATAXIAS

(71) Applicant: NATIONAL TAIWAN NORMAL UNIVERSITY, Taipei (TW)

(72) Inventors: Guey-Jen Lee-Chen, Taipei (TW); Chiung-Mei Chen, Taipei (TW)

(73) Assignee: NATIONAL TAIWAN NORMAL UNIVERSITY, Taipei (TW)

( * ) Notice: Subject to any disclaimer, the term of this patent is extended or adjusted under 35 U.S.C. 154(b) by 499 days.

(21) Appl. No.: 14/996,271

(22) Filed: Jan. 15, 2016

(65) Prior Publication Data
US 2017/0000835 A1 Jan. 5, 2017

(30) Foreign Application Priority Data

Jun. 30, 2015 (TW) .............................. 104121047 A

(51) Int. Cl.
*A61K 36/65* (2006.01)
*A61K 36/484* (2006.01)

(52) U.S. Cl.
CPC ............ *A61K 36/65* (2013.01); *A61K 36/484* (2013.01)

(58) Field of Classification Search
None
See application file for complete search history.

(56) References Cited

U.S. PATENT DOCUMENTS

2003/0211178 A1* 11/2003 Xia ....................... A61K 35/62
424/735

* cited by examiner

*Primary Examiner* — Aaron J Kosar
(74) *Attorney, Agent, or Firm* — Bacon & Thomas, PLLC

(57) ABSTRACT

The present invention relates to a method for treating spinocerebellar ataxias comprising administering a pharmaceutical composition comprising of therapeutically effective amounts of *Paeonia lactiflora* and *Glycyrrhiza uralensis* to a subject in need. The pharmaceutical composition reduces productions of reactive oxygen species and inflammatory factors to suppress polyglutamine aggregation.

11 Claims, 5 Drawing Sheets

METHOD FOR TREATING SPINOCEREBELLAR ATAXIAS

CROSS REFERENCE TO RELATED APPLICATION

This application claims the benefits of the Taiwan Patent Application Serial Number 104121047, filed on Jun. 30, 2015, the subject matter of which is incorporated herein by reference.

BACKGROUND OF THE INVENTION

1. Field of the Invention

The present invention relates to a method for treating spinocerebellar ataxias (SCAs), comprising an administration of a pharmaceutical composition comprising *Paeonia lactiflora* and *Glycyrrhiza uralensis*, which can reduce production of reactive oxygen species (ROS) and inhibit expressions of inflammatory factors, such as nitrogen oxide (NO), tumor necrosis factor-α (TNF-α), interleukin-1β (IL-1β), and interleukin-6 (IL-6), to suppress polyglutamine (polyQ) aggregation.

2. Description of Related Art

SCAs, also referred as spinocerebellar atrophy or spinocerebellar degeneration, are complex heterogeneous autosomal dominant neurodegenerative disorders. SCAs are caused by expanded CAG repeats coding long polyQ tracts, resulting in mutant proteins. The misfolded polyQ proteins accumulate in the nuclei and cytoplasm of nerve cells. The clinical symptoms of SCAs include cerebellar degeneration as well as dysfunctions of other parts of nervous system.

So far, no commercial drug is available for curing or mitigating progressive cerebellar ataxia whose symptoms are irreversible. At the beginning, patients cannot properly control their movements. As the disorder progresses, patients gradually become unable to walk, pick up a pen, and eventually unable to speak and swallow. In the worst case scenario, patients will die. While the cerebellum, brainstem, and spinal cord will become atrophic, normal functions of the cerebral cortex and intelligence are usually not affected. Thus, patients can clearly realize the fact that they are progressively losing physical control.

Up to now, there is no effective treatment to prevent the SCAs disease progression, or improve the symptoms. As a result, many people are now turning to traditional Chinese medicines as they are relatively milder in side effects.

As the global population suffering from cerebellar atrophy gradually increases, a pharmaceutical composition for treating cerebellar ataxia is needed to effectively delay disease progression and provide better life quality to patients.

SUMMARY OF THE INVENTION

An object of the present invention is to provide a method for treating SCAs that can effectively delay disease progression and serve as an adjuvant therapy of SCAs.

Another object of the present invention is to provide a method for inhibiting polyQ aggregation that can also be used by other abnormal polyQ-mediated diseases.

To achieve the above objects, the present invention provides a method for treating SCAs, comprising: administering a pharmaceutical composition comprising therapeutically effective amounts of *Paeonia lactiflora* and *Glycyrrhiza uralensis* to a subject in need. The pharmaceutical composition may be a Chinese medicine comprising *Paeonia lactiflora* and *Glycyrrhiza uralensis* manufactured by methods well-known in the art. For example, an extract of *Paeonia lactiflora* and *Glycyrrhiza uralensis* may be obtained by water extraction under heating and by filtration of dregs. However, the present invention is not limited thereto. The pharmaceutical composition formed from the extract of *Paeonia lactiflora* and *Glycyrrhiza uralensis* may be processed into a dried extract by using any conventional technique, such as spray drying, freeze drying, and scientific Chinese herbal medicine granulation. The dried extract may then be further processed into a health food or a clinical therapeutic pharmaceutical for the prevention and treatment of SCAs. In addition, the Chinese medicine comprising *Paeonia lactiflora* and *Glycyrrhiza uralensis* may be purchased from the market. The weight ratio of *Paeonia lactiflora* to *Glycyrrhiza uralensis* is not particularly limited and may be in a range from 1:2 to 2:1 such as 1:2, 1:1, and 2:1, but preferably in a range from 1:1.5 to 1.5:1 such as 1:1.

The pharmaceutical composition has radical-scavenging and anti-inflammatory abilities. As SCAs, which are one group of the polyQ-mediated diseases, are mainly a result of misfolded polyQ causing free radical production and accumulation of abnormal proteins. Hence, the pharmaceutical composition reduces the accumulation of polyQ by reducing free radical production. The pharmaceutical composition also suppresses inflammatory response by reducing productions of nitrogen oxide (NO), tumor necrosis factor-α (TNF-α), interleukin-1β (IL-1β), and interleukin-6 (IL-6). However, the present invention is not limited thereto. The pharmaceutical composition may inhibit polyQ aggregation through another mechanism.

In the present invention, since the pharmaceutical composition is able to reduce polyQ accumulation; therefore, the pharmaceutical composition may also serve as an adjuvant therapy for other abnormal polyQ-mediated diseases. Examples of the abnormal polyQ-mediated diseases include Huntington's disease, spinal and bulbar muscular atrophy, dentatorubropallidoluysian atrophy, and preferably cerebellar atrophy. However, the present invention is not limited hereto. Seven types of cerebellar atrophy are known to be caused by expanded CAG repeats coding polyQ, which are SCA1, SCA2, SCA3, SCA6, SCA7, SCA8, and SCA17. These SCAs associated with expanded polyQ show selective and progressive degenerations of cerebellum, brainstem, and spinal cord. Specifically, in degenerated nerves, expanded polyQ proteins significantly accumulate in the nuclei and cytoplasm of nerve cells, resulting in dysfunction and degradation of some specific nerve cells.

The concentration of the aforementioned pharmaceutical composition is not particularly limited and can be adjusted depending on different requirements (for example, disease severity or co-medication). In an embodiment of the present invention, the pharmaceutical composition preferably has a concentration of 0.01 μg/mL to 2 mg/mL, more preferably 0.01 μg/mL to 0.5 mg/mL, and most preferably 0.01 μg/mL to 10 μg/mL.

The present invention further provides a method for inhibiting polyQ aggregation in a subject, comprising: administering a pharmaceutical composition comprising therapeutically effective amounts of *Paeonia lactiflora* and *Glycyrrhiza uralensis* to the subject.

The term "reduce" or "reduction" refers to cases when the pharmaceutical composition of the present invention is applied to a subject suffering from SCA, toward or having symptoms of SCA, mitigation and improvement of the disease and symptoms can be seen.

To implement the method of the present invention, the above-mentioned pharmaceutical composition can be administered via oral administration, parenteral administration, spray inhalation administration, topical administration, rectal administration, nasal administration, sublingual administration, vaginal administration, or implanted reservoir, and so on. The term "parenteral" refers to subcutaneous injection, intra-dermal injection, intra-venous injection, intra-muscular injection, intra-articular injection, intra-arterial injection, intra-articular fluid injection, intra-thoracic injection, intra-spinal cord injection, disease site injection, and intra-cranial injection, or injection techniques.

Moreover, depending on the requirement, the pharmaceutical composition of the present invention may comprise: at least one of a pharmaceutically acceptable carrier, a diluent, or an excipient in the art. For example, the pharmaceutical composition of the present invention may be encapsulated in liposome to facilitate delivery and absorption. Alternatively, the pharmaceutical composition of the present invention may be diluted by aqueous suspension, dispersion, or solution to facilitate injection. The pharmaceutical composition of the present invention may be prepared as a capsule or a tablet for storage and portability. Specifically, the pharmaceutical composition of the present invention may be formulated as a solid form or a liquid form. The solid formulation may include, but is not limited to, powders, granules, tablets, capsules, and suppositories. The solid formulation may comprise, but is not limited to, excipients, flavoring agents, binders, preservatives, disintegrants, glidants, and fillers. The liquid formulation may include, but is not limited to, water, solutions such as propylene glycol solution, suspensions, and emulsions, which may be prepared with suitable coloring agents, flavoring agents, stabilizers, and viscosity-increasing agents.

For example, a powder formulation may be prepared by mixing the pharmaceutical composition of the present invention with suitable pharmaceutically acceptable excipients such as sucrose, starch, and microcrystalline cellulose. A granule formulation may be prepared by mixing the pharmaceutical composition of the present invention with suitable pharmaceutically acceptable excipients, suitable pharmaceutically acceptable binders such as polyvinyl pyrrolidone and hydroxypropyl cellulose. This is either followed by a wet granulation method using a solvent such as water, ethanol, isopropanol, or a dry granulation method using compression force. A tablet formulation may be prepared by mixing the granule formulation with suitable pharmaceutically acceptable glidants such as magnesium stearate, followed by tableting using a tablet machine. Accordingly, the formulation of the pharmaceutical composition of the present invention may be changed depending on different requirements.

BRIEF DESCRIPTION OF THE DRAWINGS

The above and other objects, features, and advantages of the present invention will become more apparent from the following detailed description taken in conjunction with the accompanying drawings, in which.

DETAILED DESCRIPTION OF THE PREFERRED EMBODIMENT

In the following description, numerous specific details are set forth to provide a thorough understanding of the embodiments of the present disclosure. However, one having an ordinary skill in the art will recognize that the embodiments of the disclosure can be practiced without these specific details. In some instances, well-known structures and processes are not described in detail to avoid unnecessary obscurity of the embodiments of the present disclosure.

Shao Yao Kan Tsao Tang (SK Tang)

Shao Yao Kan Tsao Tang (SK Tang) (Sun-Ten Pharmaceutical Company, Taipei, Taiwan) is a formulated Chinese medicine prepared from herbs, *Paeonia lactiflora* and *Glycyrrhiza uralensis*, with a relative weight ratio of 1:1. Twelve g *Paeonia lactiflora* and 12 g *Glycyrrhiza uralensis* were 4.2-fold concentrated and manufactured as 5.76 g extract. Next, 6.24 g of starch, cellulose powder, and magnesium stearate were added as an excipient and a lubricant. Five g extract was dissolved in 10 mL double deionized water (d.d water) followed by mixing and centrifugation (4000 rpm, 10 minutes) to obtain a supernatant for the SK Tang treatment during the following experiments. In general, the ingredients in *Paeonia lactiflora* and *Glycyrrhiza uralensis* have sedative, analgesic, antipyretic, anti-inflammatory, and muscle relaxing effects. Treatment indications of SK Tang include abdominal pain and legs/feet spasticity. SK Tang has analgesic effect.

Cell Culture

Human 293 ATXN3/$Q_{75}$-GFP cells were cultured in Dulbecco's modified Eagle's medium (DMEM) containing 10% fetal bovine serum (FBS), 5 μg/mL blasticidin, and 100 μg/mL hygromycin (InvivoGen). Human neuroblastoma SH-SY5Y cells (ATCC No. CRL-2266) were cultured in DMEM F12 supplemented with 10% FBS. Mouse RAW 264.7 macrophages and BV-2 microglia were cultured in DMEM containing 10% FBS. Cells were all cultured in a 37° C. incubator containing 5% $CO_2$.

ATXN3/$Q_{75}$ Aggregation Reduction Potential of SK Tang

293 ATXN3/$Q_{75}$-GFP cells were cultured in 96-well ($2 \times 10^4$/well) plates for 24 h and treated with different concentrations of suberoylanilide hydroxamic acid (SAHA, Cayman Chemical) (100 nM), *Paeonia lactiflora, Glycyrrhiza uralensis*, or Shao Yao Kan Tsao Tang (SK Tang) (0.01-10 μg/mL) for 8 h. Next, doxycycline (10 μg/mL, BD) and oxaliplatin (5 μM, Sigma) were added for 6 days. Cells were then stained with Hoechst 33342 (0.1 µg/mL, Sigma-Aldrich). Aggregation was then analyzed by high-content analysis (HCA) system (ImageXpressMICRO, Molecular Devices). The histone deacetylase inhibitor SAHA, known to reduce SDS-insoluble polyQ aggregates, was included for comparison.

Figure 1:
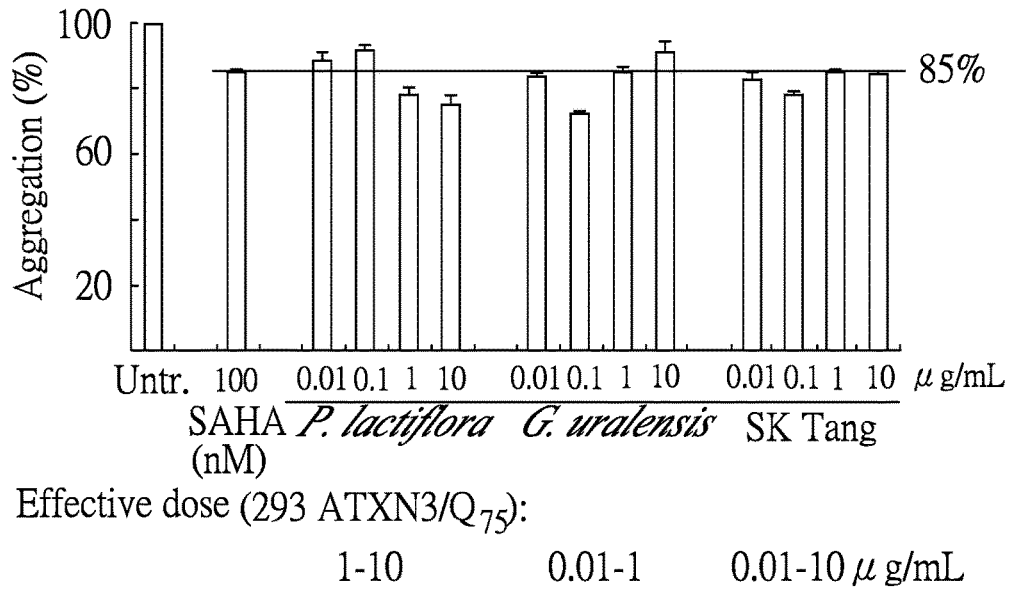
FIG. 1 shows an aggregation analysis of ATXN3/$Q_{75}$-GFP cells treated with histone deacetylase inhibitor suberoylanilide hydroxamic acid (SAHA), *Paeonia lactiflora*, *Glycyrrhiza uralensis*, or Shao Yao Kan Tsao Tang (SK Tang) according to a preferable example of the present invention.

To normalize data, the relative aggregation level in untreated cells is set as 100%. As shown in FIG. 1, the horizontal line indicates that SAHA has reduced the ATXN3/$Q_{75}$ aggregation to 85% (at 100 nM) as compared to untreated cells (100%). Good aggregation-inhibitory potential can be seen from *Paeonia lactiflora* (75-78% at 1-10 µg/mL), *Glycyrrhiza uralensis* (73-85% at 0.01-1 µg/mL), and SK Tang (79-84% at 0.01-10 µg/mL). All treatments have greater aggregation reduction potential than without treatment. Since the effective concentrations of *Paeonia lactiflora* and *Glycyrrhiza uralensis* are in narrower ranges compared to that of the SK Tang; thus, the SK Tang displays better aggregation-inhibitory potential than *Paeonia lactiflora* and *Glycyrrhiza uralensis*.

Cytotoxicity of SK Tang

The cytotoxicity of SK Tang was examined by MTT assays performed using human neuroblastoma SH-SY5Y cells after being treated by SK Tang for 24 h. SH-SY5Y cells were cultured in 96-well plates for 20 h and treated with different concentrations of SK Tang (0.1-1000 µg/mL) for 24 h. Next, 20 µL MTT (3,[4,5-dimethylthiazol-2-yl]-2,5-diphenyl-tetrazolium bromide, 5 mg/mL in PBS; Sigma-Aldrich) was added to cells followed by 2 h incubation. The absorbance of the purple formazan dye was measured at 570 nm by a Bio-Tek µQuant Universal Microplate Spectrophotometer.

Figure 2:
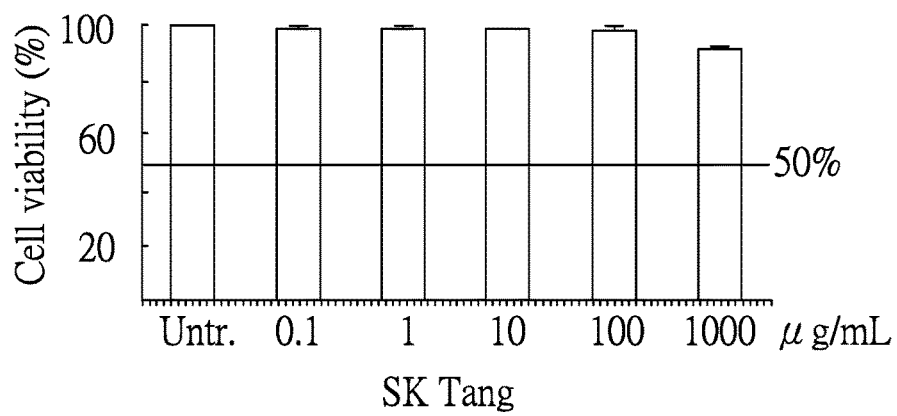
FIG. 2 shows a cytotoxicity analysis of Shao Yao Kan Tsao Tang (SK Tang) against SH-SY5Y cells according to a preferable example of the present invention.

To normalize data, the relative viability level in untreated cells is set as 100%. As shown in FIG. 2, the horizontal line indicates 50% viability. The SK Tang has a very low $IC_{50}$ cytotoxicity against SH-SY5Y cells (6.1 mg/mL). This indicates almost all SH-SY5Y cells still survive after being treated with SK Tang.

Radical-scavenging Activity of SK Tang

The radical-scavenging activity of SK Tang was examined using DPPH. 100 µM DPPH radical solution (purchased from Sigma) and 5-40 µM of kaempferol or 0.1-1.0 mg/mL of SK Tang were vortexed for 15 seconds and then left to stand at room temperature for 30 min. Next, radical-scavenging activity was measured by monitoring decrease in absorbance at 517 nm by a Thermo Scientific Multiskan GO Microplate Spectrophotometer. The radical scavenging activity was calculated using the formula: 1−(absorbance of sample/absorbance of control)×100%. The antioxidative activity was expressed as an $EC_{50}$ value, which was defined as the concentration of the SK Tang required to inhibit the formation of DPPH radicals by 50%. Kaempferol, a natural flavonol with strong antioxidant properties, was chosen as the reference antioxidant.

Figure 3:
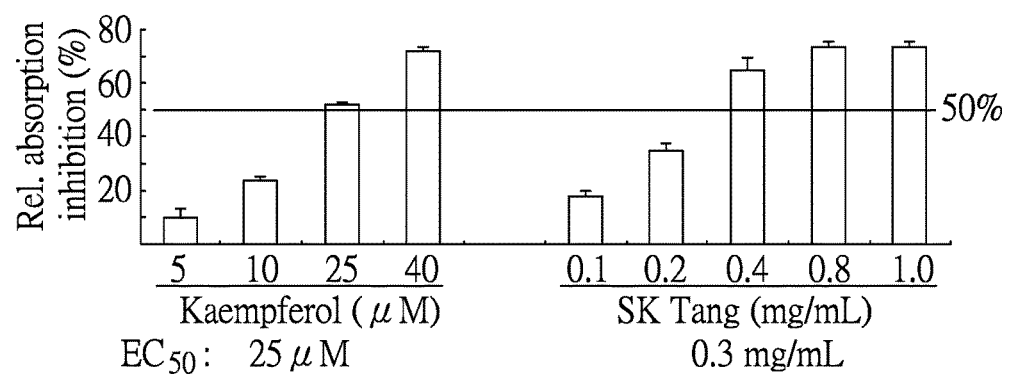
FIG. 3 shows radical scavenging activities of kaempferol and Shao Yao Kan Tsao Tang (SK Tang) on 1,1-diphenyl-2-picryl hydrazyl (DPPH) according to a preferable example of the present invention.
Figures 4A, 4B:
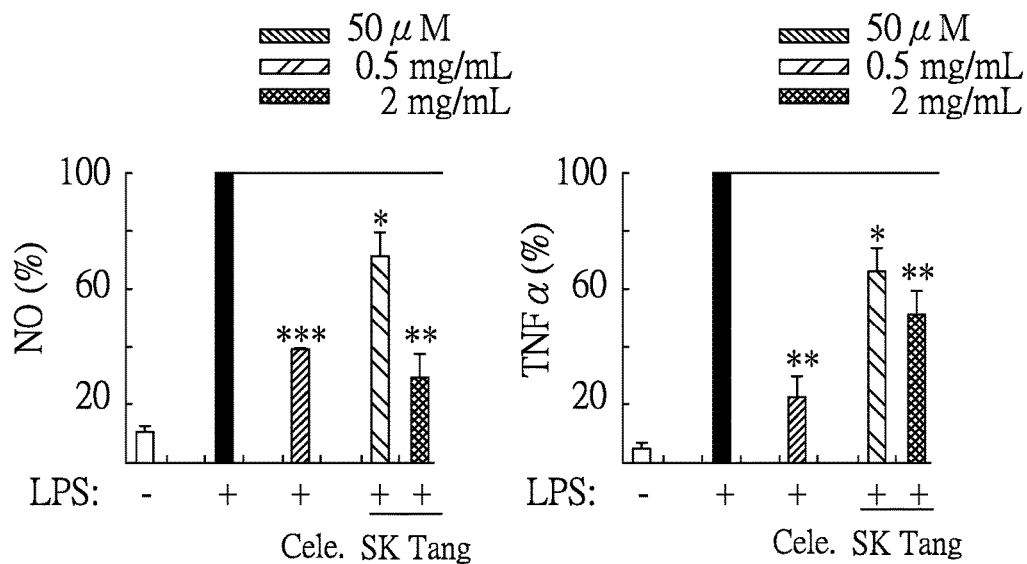
FIGS. 4A-4D respectively show secretion analyses of NO, TNF-α, IL-1β, and IL-6 in lipopolysaccharides (LPS)-stimulated RAW 264.7 macrophages treated with celecoxib and Shao Yao Kan Tsao Tang (SK Tang) according to a preferable example of the present invention.
Figures 4C, 4D:
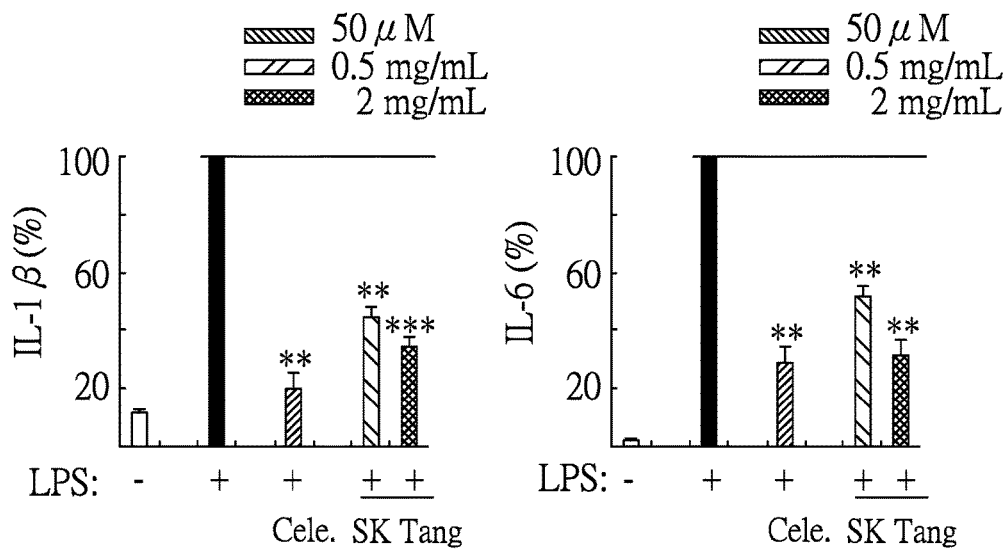

As shown in FIG. 3, the horizontal line indicates 50% DPPH-scavenging activity. Kaempferol and SK Tang have $EC_{50}$ of 25 µM and 0.3 mg/mL, respectively. Hence, the traditional Chinese medicine formula of SK Tang displays DPPH-scavenging activity.

Anti-inflammatory Activity of SK Tang

The anti-inflammatory activity of SK Tang was examined using LPS-stimulated RAW 264.7 macrophage and BV-2 microglia. RAW 264.7 cells ($10^6$) were cultured in 6-well plates for 20 h and pre-treated with celecoxib, which is a nonsteroidal anti-inflammatory drug (named as Cele. in FIGS. 4A-4D) (50 µM) or SK Tang (0.5-2 mg/mL) for 8 h. Next, cells were stimulated by LPS (1 µg/mL) for 20 h. LPS-induced secretions of NO, TNF-α, IL-1β, and IL-6 in RAW 264.7 cells were then determined using Griess reagent or ELISA assay.

To normalize data, the relative NO/TNF-α/IL-1β/IL-6 level in LPS-stimulated cells is set as 100%. As shown in FIGS. 4A-4D, the exposure of RAW 264.7 cells to LPS results in significant secretions of NO, TNF-α, IL-1β, and IL-6 after 24 h incubation (1-12% vs. 100%, P<0.001). The elevations in NO, TNF-α, IL-1β, and IL-6 production are significantly reduced in the presence of celecoxib (NO: 39%, P<0.001; TNF-α: 23%, P=0.003; IL-1β: 20%, P=0.001; IL-6: 29%, P=0.002). A similar inhibitory phenomenon is observed from cells treated with SK Tang (NO: 72-30%, P=0.023-0.004; TNF-α: 66-51%, P=0.044-0.005; IL-1β: 44-35%, P=0.002-<0.001; IL-α: 51-30%, P=0.003-0.002).

BV-2 cells ($4 \times 10^4$) were cultured in 12-well plates for 20 h and pre-treated with celecoxib (50 µM) or SK Tang (100 µg/mL and 500 µg/mL) for 8-24 h. Next, cells were stimulated by LPS (1 µg/mL) for 20 h. Levels of NO production in cultured medium were measured using Griess reagent.

Figure 5:
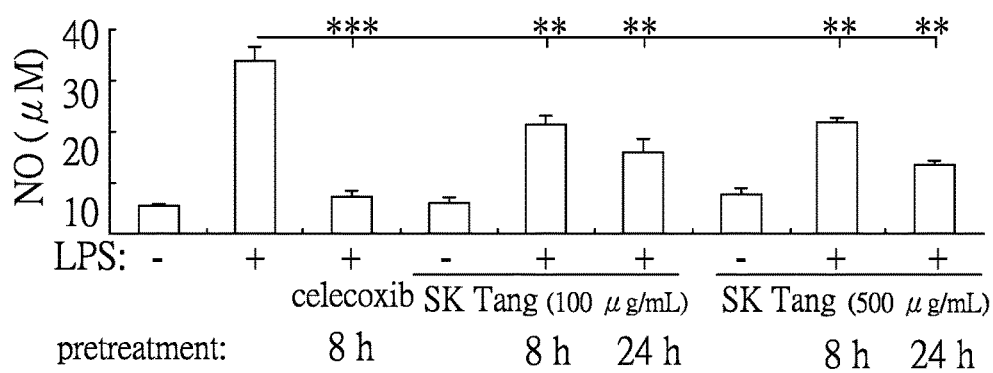
FIG. 5 shows a secretion analysis of NO in LPS-stimulated BV-2 microglia treated with celecoxib and Shao Yao Kan Tsao Tang (SK Tang) according to a preferable example of the present invention.

As shown in FIG. 5, pretreatments of BV-2 cells with celecoxib (50 µM) for 8 h (P<0.001) or SK Tang (100 µg/mL and 500 µg/mL) for 8-24 h (P=0.009-0.001) can reduce LPS-induced NO secretion.

Amelioration of Neurobehavior of SK Tang-treated SCA17 Mice

To understand whether SK Tang can improve neurobehavior of SCA17 transgenic mice, SK Tang (0.4%) was added to the drinking water of wild-type mice (named as WT-SK Tang in FIGS. 6A-6C) and SCA17 transgenic mice (named as TG-SK Tang in FIGS. 6A-6C) from 11 to 21 weeks old. For comparison, additional wild-type mice and SCA17 transgenic mice were used as control groups (respectively named as WT-Vehicle and TG-Vehicle in FIGS. 6A-6C).

Figure 6A:
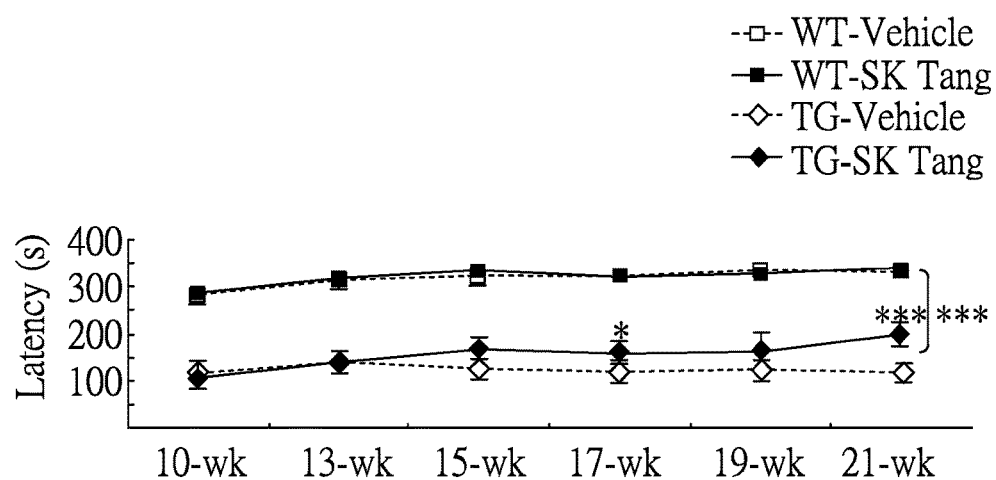
FIGS. 6A-6C respectively show a motor coordination analysis (rotarod analysis), a hyperactivity analysis (locomotor analysis), and a gait coordination analysis (footprint analysis) of SCA17mice treated with Shao Yao Kan Tsao Tang (SK Tang) according to one preferred embodiment of the present invention.

Motor coordination of SCA17 transgenic mice was examined by rotarod analysis. As shown in FIG. 6A, the latency staying on the rotarod of SK Tang-treated SCA17 transgenic mice is significantly increased at 17 (P=0.015) and 21 (P<0.001) weeks old. The highly reduced latency staying on the rotarod of SCA17 transgenic mice is ameliorated by SK Tang treatment at 17 and 21 weeks of age.

Figure 6B:
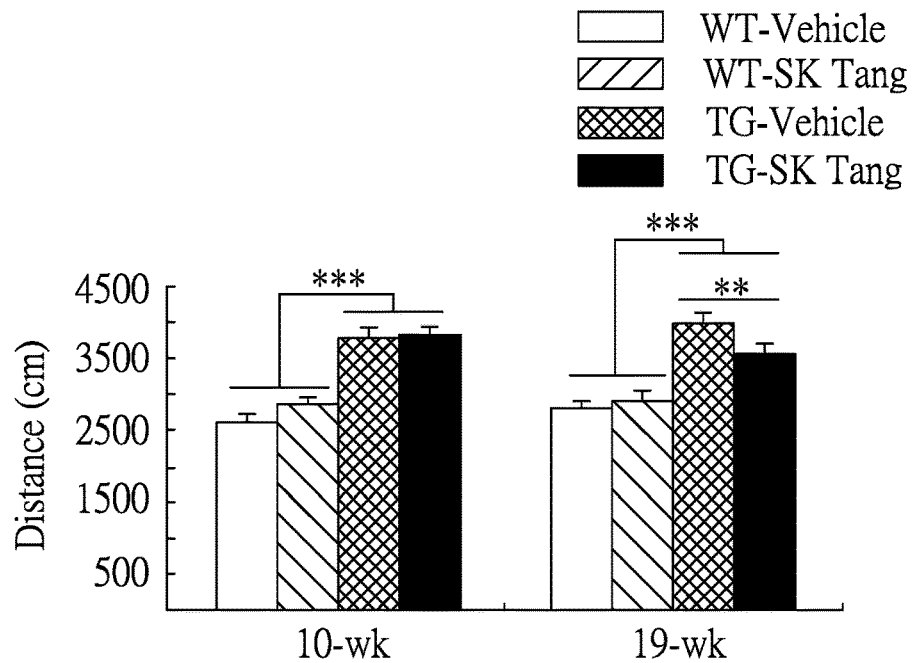

Hyperactivity of SCA17 transgenic mice was examined by locomotor analysis. Degrees of hyperactivity and anxiety of each mouse were measured as the total distance traveled in an open field (30×30 cm). As shown in FIG. 6B, SCA17 transgenic mice are generally hyperactive in an open field. However, the hyperactivity of SK Tang-treated SCA17 transgenic mice is significantly decreased at 19 weeks old (P=0.007). The high degrees of hyperactivity and anxiety of SCA17 transgenic mice are ameliorated by SK Tang treatment at 19 weeks of age.

Figure 6C:
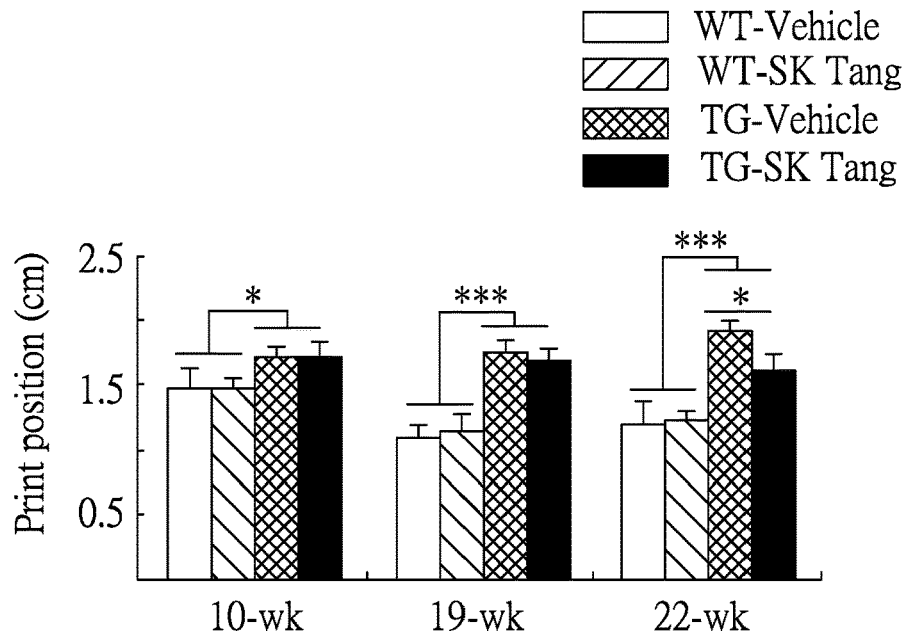

Gait coordination of SCA17 transgenic mice was examined by footprint analysis. As shown in FIG. 6C, the print position of both paws of SK Tang-treated SCA17 transgenic mice is significantly decreased at 22 weeks old (P=0.036). Gait impairment of SCA17 transgenic mice is ameliorated by SK Tang treatment at 22 weeks of age.

It should be understood that these examples are merely illustrations of the present invention. The scope of the present invention should not be construed to those defined thereby. Instead, the scope of the present invention will be limited only by the appended claims.

What is claimed is:

1. A method for treating spinocerebellar ataxias, comprising: administering a pharmaceutical composition comprising therapeutically effective amounts of *Paeonia lactiflora* and *Glycyrrhiza uralensis* to a subject in need,
    wherein a preparation of the pharmaceutical composition comprises:
        providing 50 wt % of the *Paeonia lactiflora* and 50 wt % of the *Glycyrrhiza uralensis* to form a mixture;
        concentrating the mixture to form an extract.

2. The method of claim 1, wherein the extract has a concentration of 0.01 µg/mL to 10 µg/mL.

3. The method of claim 1, wherein the pharmaceutical composition further comprises: at least one pharmaceutically acceptable carrier, a diluent, or an excipient.

4. The method of claim 1, wherein the treatment of spinocerebellar ataxias is mediated by suppressing polyglutamine aggregation.

5. The method of claim 4, wherein the treatment of spinocerebellar ataxias is mediated by reducing production of reactive oxygen species (ROS).

6. The method of claim 4, wherein the treatment of spinocerebellar ataxias is mediated by reducing productions of nitrogen oxide (NO), tumor necrosis factor-α (TNF-α), interleukin-1β (IL-1β), and interleukin-6 (IL-6).

7. A method for inhibiting polyglutamine aggregation in a subject, comprising: administering a pharmaceutical composition comprising therapeutically effective amounts of *Paeonia lactiflora* and *Glycyrrhiza uralensis* to the subject, wherein a preparation of the pharmaceutical composition comprises:
    providing 50 wt % of the *Paeonia lactiflora and* 50 wt % of the *Glycyrrhiza uralensis* to form a mixture;
    concentrating the mixture to form an extract.

8. The method of claim 7, wherein the extract has a concentration of 0.01 µg/mL to 10 µg/mL.

9. The method of claim 7, wherein the pharmaceutical composition further comprises: at least one pharmaceutically acceptable carrier, a diluent, or an excipient.

10. The method of claim 7, wherein the inhibition of polyglutamine aggregation is mediated by reducing production of reactive oxygen species (ROS).

11. The method of claim 7, wherein the inhibition of polyglutamine aggregation is mediated by reducing productions of nitrogen oxide (NO), tumor necrosis factor-α (TNF-α), interleukin-1β (IL-1β), and interleukin-6 (IL-6).

\* \* \* \* \*